United States Patent [19]
Hughes et al.

[11] Patent Number: 5,845,644
[45] Date of Patent: Dec. 8, 1998

[54] BLADDER AND BOWEL TRAINING SYSTEM

[76] Inventors: Charles B. Hughes, 3309 Lookout Dr., Huntsville, Madison County, Ala. 35801; Emory D. Hughes, 46 High Point Rd., Edgefield, Edgefield County, S.C. 29824

[21] Appl. No.: 918,455

[22] Filed: Aug. 26, 1997

Related U.S. Application Data

[60] Provisional application No. 60/025,022 Aug. 26, 1996.

[51] Int. Cl.[6] ....................................................... A61F 5/48
[52] U.S. Cl. ............................................ 128/885; 128/886
[58] Field of Search ..................................... 128/885, 886, 128/869; 340/573, 539, 604, 620

[56] References Cited

U.S. PATENT DOCUMENTS

| | | | |
|---|---|---|---|
| 3,971,371 | 7/1976 | Bloom | 128/886 |
| 4,106,001 | 8/1978 | Mehoney | 128/886 |
| 4,191,950 | 3/1980 | Levin | 128/886 |
| 4,205,672 | 6/1980 | Dvorak | 128/886 |
| 5,416,469 | 5/1995 | Colling | 128/886 |
| 5,709,222 | 1/1998 | Davallou | 128/886 |

*Primary Examiner*—Michael A. Brown
*Attorney, Agent, or Firm*—Mark Clodfelter

[57] ABSTRACT

A bowel and bladder training system is provided. A sensor strip is constructed of a tissue paper-type or other woven or sheet material having conductive sensor threads longitudinally positioned in the strip. A pocket may be formed at one end of the strip for holding a microprocessor-based indicator which is coupled to the sensor threads. The microprocessor may have several modes of operation including a vibration mode, an audio mode, and a visible mode, these modes activated when the sensor threads are bridged by bodily fluids containing electrolytes. Additionally, one of the modes may activate a voice module that is replacable or rerecordable with a personalized instructional or educational message.

8 Claims, 12 Drawing Sheets

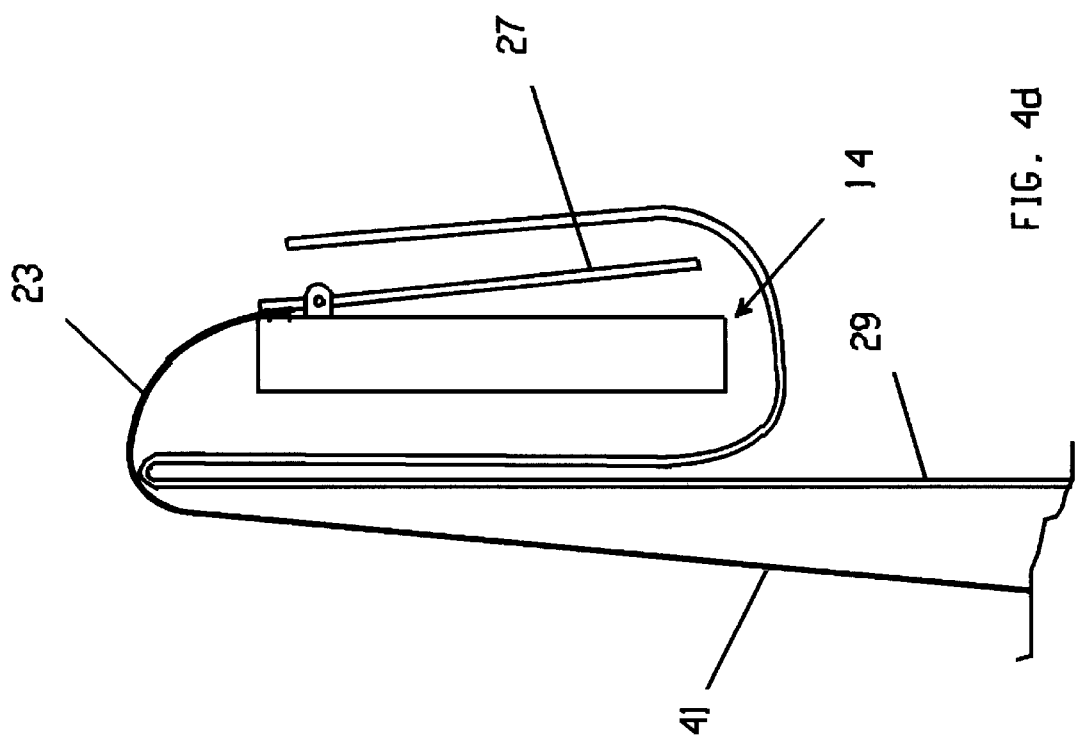

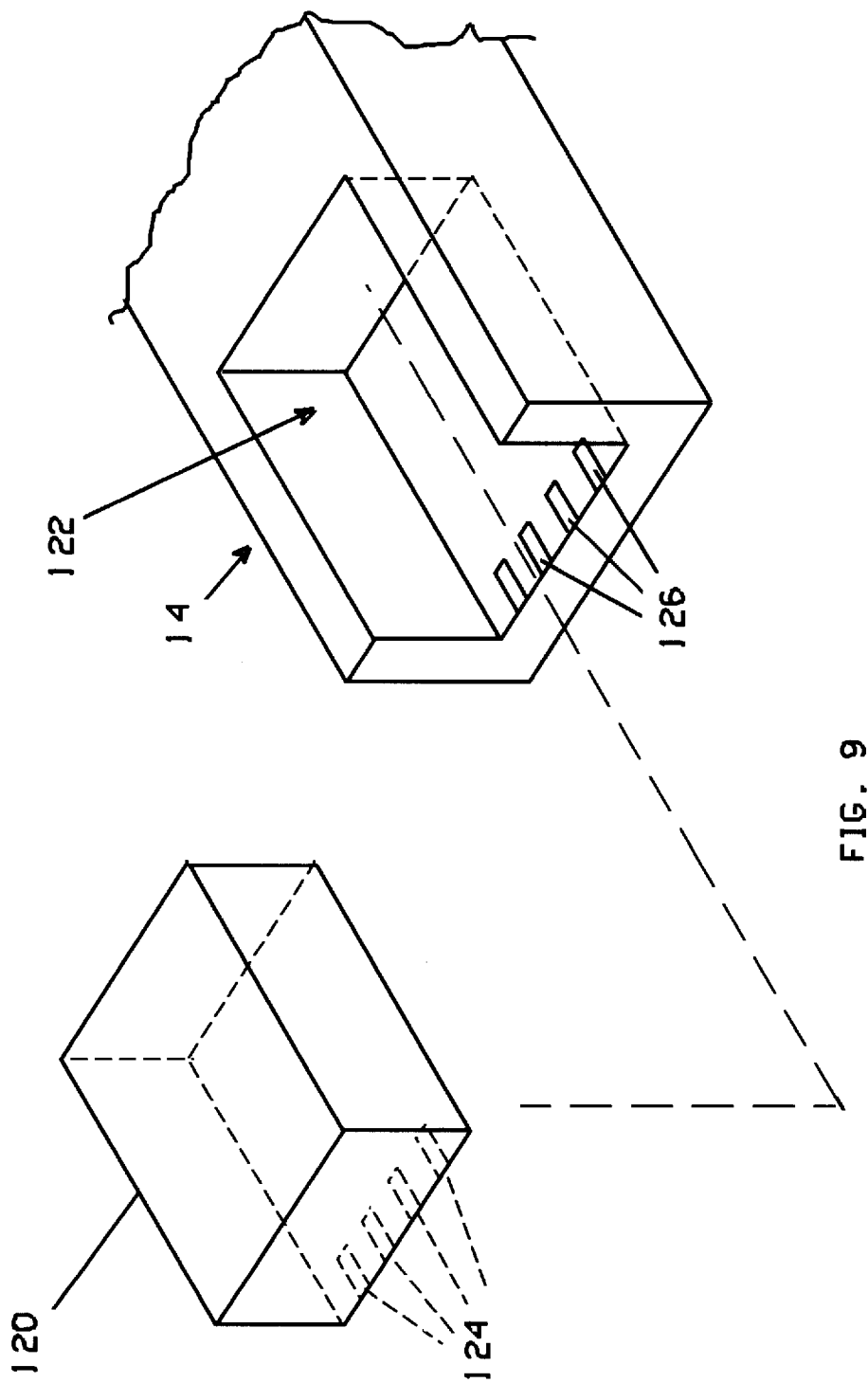

BLADDER AND BOWEL TRAINING SYSTEM

CONTINUING APPLICATION DATA

This application is a continuation-in-part of Provisional patent application Ser. No. 60/025,022, filed Aug. 26, 1996.

FIELD OF THE INVENTION

This invention relates to training aids for training or retraining of bladder and/or anal sphincter muscles of the 20 million or so individuals in the United States who suffer from incontinence. More particularly, this invention utilizes a disposable, inexpensive carbon impregnated sensor thread in a sensor strip that allows consideration of reusable cloth diapers and inserts which greatly reduces skin disorders and bladder infections while offering the advantage of cost reduction and conservation of space in landfills.

BACKGROUND OF THE INVENTION

Incontinence is a urologic disorder that results in partial or full loss of control of anal and/or bladder sphincter muscles, reducing or eliminating control over fecal and urine flow, respectively. The American Foundation for Urological Disease (AFUD) reports that more than 50 million individuals suffer from traumatic urologic disorders, of which the National Association for Continence (NAFC) documents 20 million suffering from incontinence. Some of these individuals are in nursing homes or hospitals, while others are ambulatory to the point of leading normal lives with the exception of being affected by incontinence.

Incontinence sufferers are generally classified in three major groups; ambulatory adults, geriatric bedridden and juvenile. Specialized treatment is required for each group, with surgery being predominant for ambulatory adults and the geriatric, followed by medication, exercises of the muscles of the pelvic floor, biofeedback, electrical stimulation, and collagen injection. The associated cost of such treatments amounts to something on the order of about 13 billion dollars annually, with much of this cost being borne by Medicare. The National Association for Continence 1996 Spring report, Volume 14, #2 reports the following results after treatment:

2.6% report being cured 9.4% report having a worse condition 41.4% report slight to moderate to greatly improved conditions 46.6% report no change in condition From treatment results, the Medicare burden is completely removed in only 2.6% of cases while 97.4% of these cases remain a financial burden.

At the American Urological Association Allied authored by Jan O'Dea of Columbous Urology Inc. of Columbous, Ohio is quoted as stating "Our private urology practice has treated 21 men with incontinence after radical prostatectomy for localized prostate cancer. 20 of the 21 patients demonstrated improvement, with the majority reporting 75% to 100% satisfaction. 6 patients are totally pad free. Patients began treatment from 3 to 5 years after prostatectomy and had varying degrees of incontinence. Treatment consisted of a comprehensive approach using behavorial interventions and biofeedback assisted pelvic floor exercises". Biofeedback is a scientific technique wherein an individual consciously controls a bodily function, such as heartbeat, blood pressure, or certain sphincter muscles, responsive to signals provided by instrumentation. Such instrumentation typically uses adhesive skin patches or straps incorporating electrical terminals that gather electrical information from skin of the patient, and which are manufactured by a number of manufacturers today. In addition, HUMED of Huntsville, Ala., has developed an affordable, portable application specific home/office biofeedback training system to serve an array of patient disorders including depression, incontinence, stress, and stroke. Success is repetitive dependent, necessitating a portable in-home unit. Applicants system includes a portable computer similar to a laptop computer having a display, sensor package, CD ROM drive, and prerecorded memory voice modules. Accordingly, a patient visits a hospital, clinic, pain center, or other appropriate institution to be evaluated as to specific needs. Upon a determination that Applicants system is an appropriate treatment, the patient is provided the system along with a CD ROM and voice module containing information specific to his/her needs. After a predetermined period of time, the patient revisits the institution for evaluation of progress, at which point the patient may be given another CD ROM and voice module containing different instructions to further treatment. As such, one objective of the instant invention is to offer affordable training or retraining of the bladder and/or anal sphincter muscles that have been impaired by stroke, Alzheimers disease, prostrate disorders, surgery, child birth, medication side effects, aids, behavioral disorders, learning disabilities and other conditions that necessitate training or retraining of muscles that control voiding of the bowel and bladder.

Aside from the ever present danger of skin and bladder infections, incontinence may rob the individual of self confidence, sleep, extended travel, the joy of physical activity, and often reduces an individual to a disabled condition. This sometimes occurs where an individual uses a gel-type incontinence garment or insert, which garments and inserts being designed to hold a greater quantity of liquid than a non-gel type garment or insert. As a result of the greater capacity of these gel-type devices, a user may become accustomed to the odor of urine, and in turn becoming unaware of the discomfort of others subjected to such odor. The ensuing embarrassment from this situation often drives an individual to become reclusive, in turn placing additional burdens on the state and federal governments, whereas with proper training or retraining of the bowel and bladder sphincter muscles, many of these conditions may be reduced or eliminated, allowing a disabled individual to resume a normal life.

In addition, over 19 billion gel-type diapers, inserts and other incontinence garments are used annually, and occupy a significant proportion of landfill space. The materials in these diapers, inserts and disposable garments require something on the order of about 200 years to decompose. Applicants sensor strip may be constructed of readily decomposable materials, allowing use of non-disposable undergarments or diapers which may be washed.

A number of incontinence alarms for ambulatory adults, geriatric bedridden and juveniles have been proposed but all are significantly different from Applicants bladder and bowel training system, and none have enjoyed any significant measure of success. One reason for the lack of success of these prior art alarms may be that most disposable pads used for incontinence alarm systems are cumbersome to wear and difficult to connect. Another reason may be expense of the alarm and disposable pads, which may be considerable where each disposable pad is provided with leads that are connected to a sensor element in the pad, with terminals at the end of the leads for connection to the alarm. Yet another reason may be that many individuals with urinary incontinence tend to "dribble", or constantly leak urine at the same rate as kidney production. In this instance, it is simply too expensive and time consuming to constantly change incontinence garments. As a result, these individuals often simply change their incontinence garments at set times during their waking hours. The problem with this is that the kidneys produce urine at varying rates, meaning that an incontinent individual may ignore a saturated incontinence garment too long, promoting skin rashes or ulceration of the skin. On the other hand, the incontinence garment may be changed before becoming sufficiently wetted to warrant changing, resulting in waste and the attendant cost.

Another problem is that in those devices wherein a sensor strip is used to sense a wet condition of an incontinence garment, such as in U.S. Pat. No. 5,226,928, issued to Johnson, the sensor strip is constructed of a non-variable length. As such, the strip must be long enough to insure adequate length for all individuals. Additionally, due to configuration of the alarm circuitry, shortening the sensor strip would, in one embodiment where a urine battery is formed by the length of the conductors, decrease current provided by the urine battery to a point where the alarm probably would not operate. In the other embodiment, shortening the sensor strip would decrease the available conductor length over which a preselected resistive threshold is established, adversely affecting operation of the alarm.

It is believed that other products were not successful because they were designed, developed and marketed exclusively as alarm systems without the ability to train or retrain bladder and anal sphincter muscles. Patent references include U.S. Pat. No. 5,226,928 to Johnson as discussed above; U.S. Pat. No. 4,977,906 issued to Disciple, and is intended to be used in conjunction with supervision; U.S. Pat. No. 4,162,490 issued to Hung-Fa is a device affixed to a toilet seat; U.S. Pat. No. 5,043,704 to Blakney and discloses a bed wetting alarm; U.S. Pat. No. 4,356,479 to Wilson, and is a bed wetting detector; U.S. Pat. No. 5,036,859 to Brown, and discloses a bed wetting detector device; and U.S. Pat. No. 4,796,014 issued to Cala, and activates an alarm that incorporates a time delay so as to not interrupt the act of urination by a baby.

Applicants bladder and bowel training system fulfills all requirements of an affordable, portable, non-invasive, self-contained training system designed to allow the incontinence sufferer to conceal an electronic alarm package having a number of modes of operation anywhere on his/her person. These modes of operation include audible, mechanical, transmitted, verbal, and visible modes that alert a user to inadvertent flow of urine and fecal material. Concealment of the electronics package may be accomplished simply affixing the electronics package to the front or rear of a diaper or incontinence garment, or the electronics package may be contained in a separate pocket pinned or clipped to clothes of the user. Also, the electronics package may be carried in a pocket of a garment worn by the user, such as a shirt pocket, thereby facilitating a more normal lifestyle of an affected individual. Such concealment is important inasmuch as Applicants system allows the incontinence sufferer to develop self confidence knowing that the system does not draw attention to the individual's disorder. Also, design of Applicants system allows it to be constantly worn in comfort by a user for the purpose of biofeedback training and development of self confidence.

Accordingly, it is an object of the invention to provide a urinary sensor strip for use by an incontinent individual that is of linear construction and which in operation is insensitive to length. Another object is to provide a urinary sensor strip relatively insensitive to dribbling, which accordingly provides indications only when the incontinence garment needs changing. Yet another object is to provide circuitry which implements a variety of modes of operation depending on needs of the user.

SUMMARY OF THE INVENTION

A bowel and bladder training system provides a generally rectangular pad which may have a pocket at one end, with a pair of sensor threads fixed longitudinally in the pad. The pocket contains an indicator unit coupled to the sensor threads and controlled by a microprocessor further having a storage register containing a program for providing modes of operation including a vibrating indication, an audio indication, and a visible indication. These modes of operation are responsive to electrolytes in bodily fluids bridging the sensor threads, which provides power to the mocroprocessor. When the pad is replaced, power is removed from the microprocessor, resetting the microprocessor in preparation for again indicating an incontinent condition.

BRIEF DESCRIPTION OF THE DRAWINGS

FIG. 4d is a broken away view of the sensor strip of FIG. 4c and indicator unit in use.

FIG. 9 is an illustration of a removable voice module of the instant invention.

FIG. 10 is an illustration of indicator unit 14 incorporatable in a fishing lure.

DETAILED DESCRIPTION OF THE DRAWINGS

Figure 1:
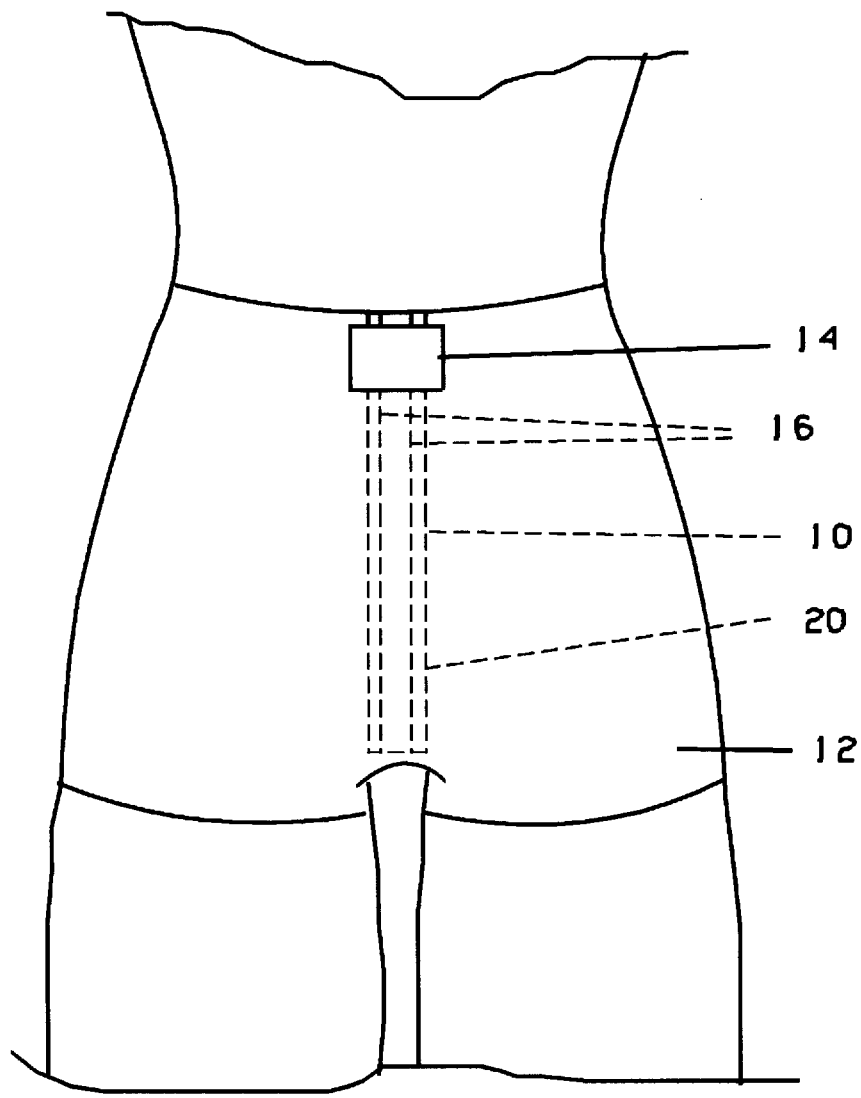
FIG. 1 is an illustration of a user wearing an incontinance garment and sensor strip and indicator unit of the instant invention.

Referring initially to FIG. 1, a view of the instant invention is shown in one of its contemplated uses. Here, a disposable sensor strip 10 (dashed lines) of appropriate length as adjusted for size of a user is positioned between the perianal area of the user and incontinence garment 12. While shown in use with a full-size incontinence garment, strip 10 may also be used in conjunction with incontinence inserts and conventional undergarments and underwear. An electronics package 14 implements various modes of operation to alert the user that voiding is occurring or that the incontinence garment requires changing, as determined by the user. Sensor strip 10 is linearly constructed of an inexpensive, thin, porous substrate material 20 such as a tissue-type paper, cloth, spun or woven material, non-porous sheet material or combinations thereof.

Figure 2A:
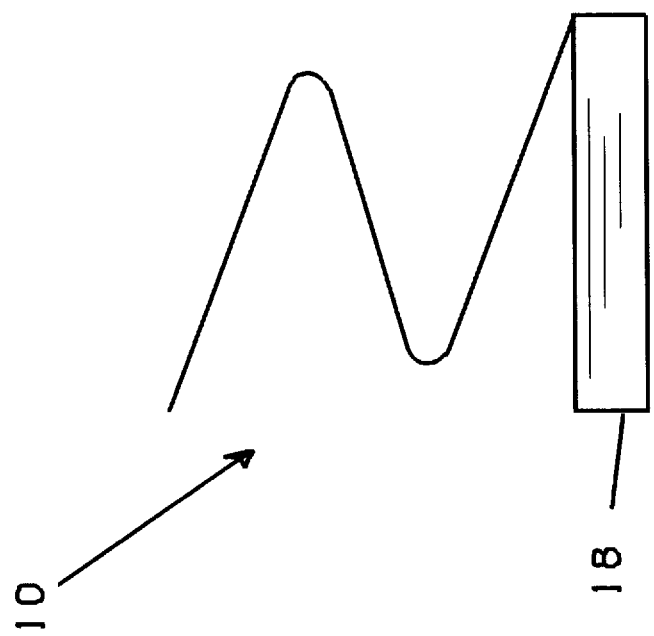
FIG. 2a is an illustration of a length of sensor strip material containing a number of sensor strips packaged in a flat package suitable for carrying in a pocket or purse.
Figure 2:
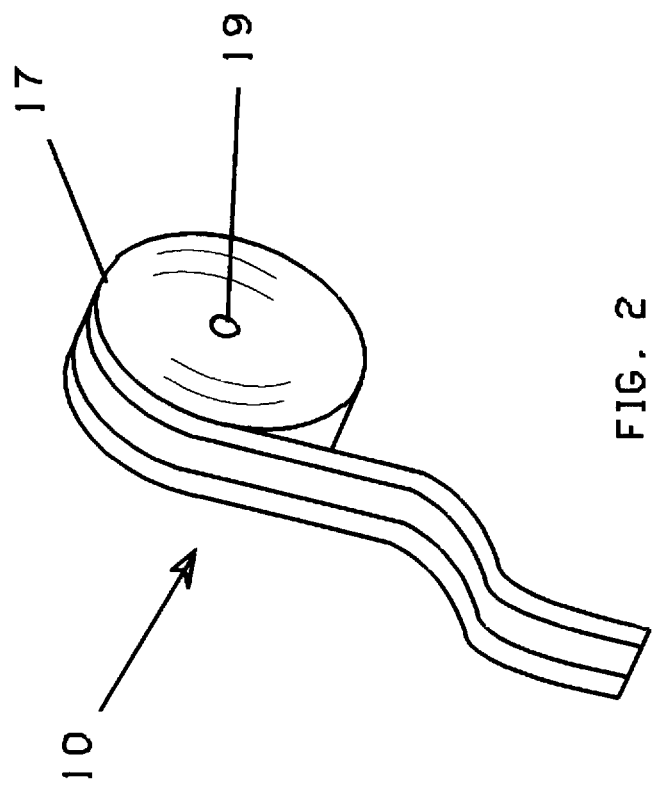
FIG. 2 is an illustration of a roll of sensor strip material suitable for a dispenser and containing a number of sensor strips.

A pair of spaced threads 16 of relatively strong, flexible material, such as cotton, flax, rubber, or a synthetic material, are made electrically conductive as by the addition of a conductive material, such as, but not limited to, carbon. Such conductivity of threads 16 may be of any degree as long as an electrical path created by electrolytes in urine of fecal material bridging threads 16 is detectable by circuitry in unit 14. These conductive threads are available from HUMED INC. located in Huntsville, Ala., and form conductive sensor elements that are stitched or otherwise imbedded, as by adhesive, lengthwise into the substrate material 20. Garment 12 may be in the form of a conventional undergarment, diaper, or the like used to catch and absorb urine or fecal material of an incontinent individual. Threads 16 in sensing strip 10 serve to sense a wet condition of garment 12, and initiates a variety of alerting responses from electronic package 14 clipped to strip 10. Significantly, as morphology between individuals varies greatly, and as there are no mechanical or electrical length restrictions on the sensor strip, sensor strip 10 may be constructed as a continuous strip and conveniently packaged in a form, such as on a roll 17 or in a flat package 18, as shown in FIGS. 2 and 2a, respectively, which allows the user to simply tear or cut an appropriate length of sensing strip material from a contiguous, packaged length thereof. As such, sensor strip 10 may be field fashioned to accommodate individual needs by selectively cutting a desired length from roll 17 or flat package 18 of sensor strip material. For example, an infant may require a sensing strip of only a few inches in length to extend from the top of the diaper to a point such that the sensing strip completely traverses the perianal area, while a large adult of substantial girth may require a sensing strip three feet or more in length in order for the sensor strip to provide coverage of the same perianal area. Where the sensor strips are fabricated on roll 17, they may be placed inside a dispenser (not shown) which rotatably supports roll 17 about an axis 19 and which may incorporate a knife edge or other cutting assembly to facilitate cutting a selected length of sensor strip material to form a single sensor strip. This arrangement may be preferable for use in institutions such as hospitals, nursing homes and Veterans Administration Hospitals, where rolls 17 of sensor strip material sized such that numerous, possibly hundreds, of sensor strips may be obtained from a single roll installed in discrete patient rooms or in a central location. As such, and as an important feature of the instant invention, the sensor strips may be sized in length according to individual needs of each patient, eliminating waste related to sizing of the sensing strips. Additionally, by constructing the sensor strips as continuous lengths from which a plurality of sensing strips may be obtained and packaging them on a roll, manufacturing of the strips is greatly simplified, with attendant reduction in manufacturing costs. Alternately, a sensor strip 10 may be incorporated as a part of an existing or developed incontinence garment or insert or appropriate undergarment. In this embodiment, sensor strip 10 may be sewed directly into an incontinence garment, insert or undergarment, with a covering to shield the conductive threads from skin of the user. A tongue or flap of material containing the conductive threads would be provided in a convenient location, such as the front of the garment, so as to facilitate connection to electronic package 14. Also, two conductive threads may be sewed directly into an incontinence garment, insert or undergarment with a tongue or flap of material containing the threads provided as described.

The disposable sensor strip is designed for use with all diapers and inserts and all appropriate undergarments. Also, where sensor strip 10 is constructed of paper tissue-type materials, strip 10 may be disposed in most conventional septic systems. In other instances, sensor strip 10 may allow use of inexpensive non-gel incontinence garments and inserts, which reduce the likelihood of skin disorders and bladder infections while reducing waste deposited in landfills. Of course, gel-filled incontinence garments may be used where necessary.

Figure 3:
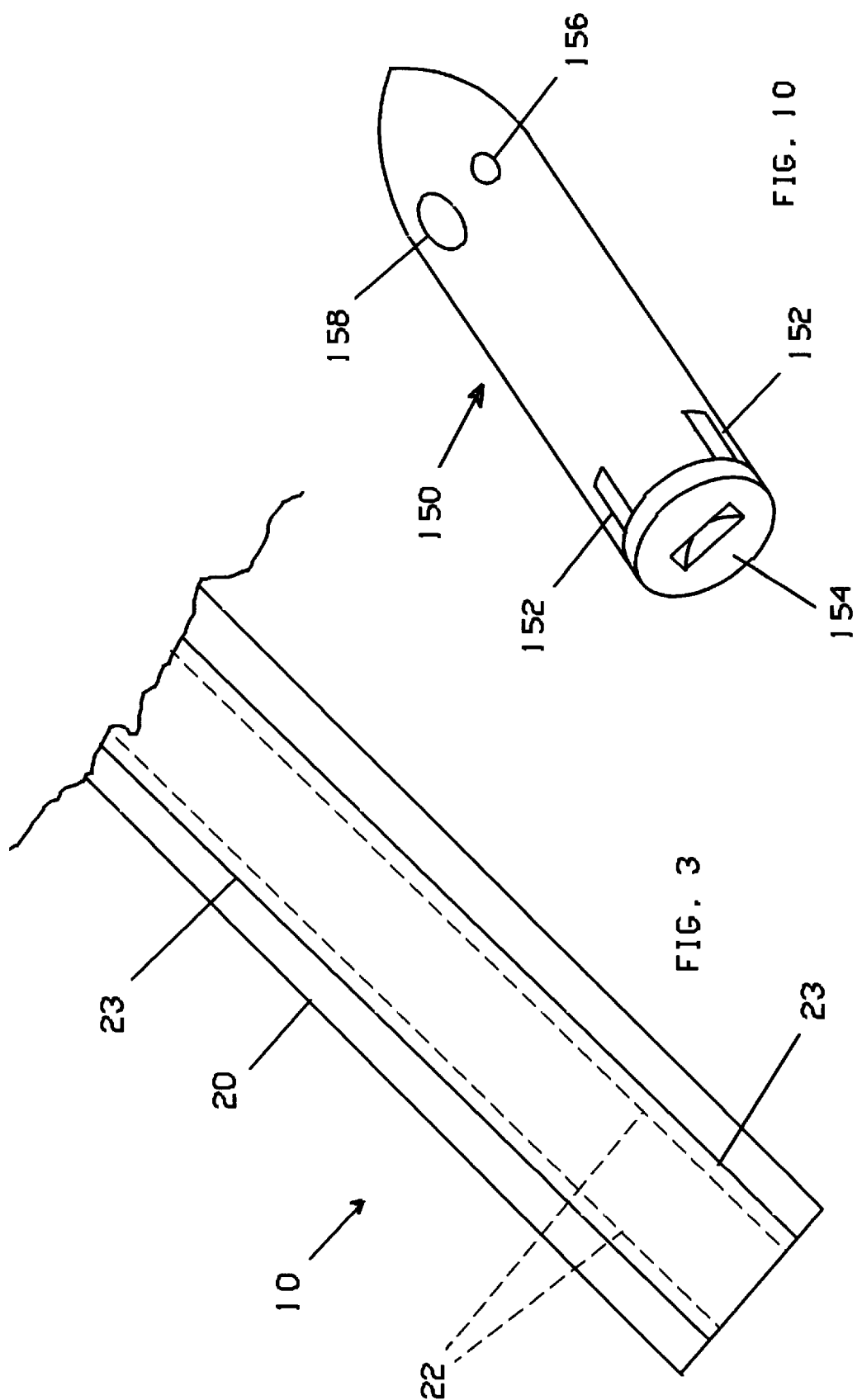
FIG. 3 is an illustration of details of construction of sensor strip material.

Sensor strip 10, as contemplated in one embodiment thereof, is constructed having a substrate width of about 4.5 inches. For packaged lengths containing sufficient strip material to fashion a number of sensor strips therefrom, the substrate length may be about 10 feet or more. As described above, and as shown in FIG. 3, substrate 20 is provided with two spaced, conductive threads 22 which are sufficiently flexible so as to be sewn or stitched lengthwise as shown into substrate 20, or imbedded in the substrate material by other means, such as by an adhesive or strip of material which secures the threads to substrate 20. Threads 22 may be spaced from about 1 to 3 inches apart, and edges of substrate 20 outboard the threads may be folded generally along lines 23 and secured on a side of the substrate material opposite threads 22, covering threads 22 on that side. In use, the exposed sensor threads are positioned adjacent the incontinence garment, with the folded-over edges positioned next to the skin of the user. Electronics package 14 may be provided with a spring-loaded clip 30, as shown in FIG. 4a, with a pair of contacts 34 underneath a clamping portion 32 of clip 30 for contacting the respective threads of a selected length of sensor strip material when sensor strip 10 is clamped by clamping portion 32. The spring force of clip 30 may be selected such that clamping portion 32 clamps strip 10 with sufficient force such that no other support is required for electronics package 14. In this application, and where the sensor strip is constructed of sufficiently strong material, electronics package 14 may simply hang freely, or otherwise be carried in a shirt or other garment pocket 31 in outer garment 33 by cutting an extended-in-length sensor strip 35 which is worn beneath outer garment 33 and routed to unit 14 via a slit 37 in the clothing material behind the pocket or a pocket liner. Also, a separate pouch (not shown) may be provided for holding electronics package 14, which pouch being pinned or clipped at an appropriate location to clothing or incontinence garment of the user and having a suitable slit or opening for receiving sensor strip 10. Other variants of the sensor strip include coating a side of the strip worn next to the skin with medication, salves, or deodorant substances, such as sodium bicarbonate, and providing an adhesive backing to the strip to prevent the strip from shifting in the incontinence garment.

In the instance where an individual or patient has an incontinent condition that causes "dribbling", a continuous or briefly intermittent small spillage of urine, it is desirable not to activate a signal until the incontinence garment needs to be changed. In this instance, spacing of threads 20 may be increased from a normal separation of from about 1–3 inches to a wider separation so that a larger area of the incontinence garment or insert must be wetted in order to initiate a response from electronics package 14. In another embodiment, strip 10 may be provided with a selected amount of hydrophobic compound to repel moisture until the incontinence garment needs changing, or a liquid impervious backing may be used so that liquid activating package 14 is forced to seep around edges of the strip 10. Alternately, time delays may be incorporated in electronics package 14 to delay activation of any alert signal for a predetermined duration, such as one hour, two hours, three hours, etc. This time delay would provide adequate time for the incontinence garment to become sufficiently wetted prior to alerting the user that it needs to be changed.

Figure 4:
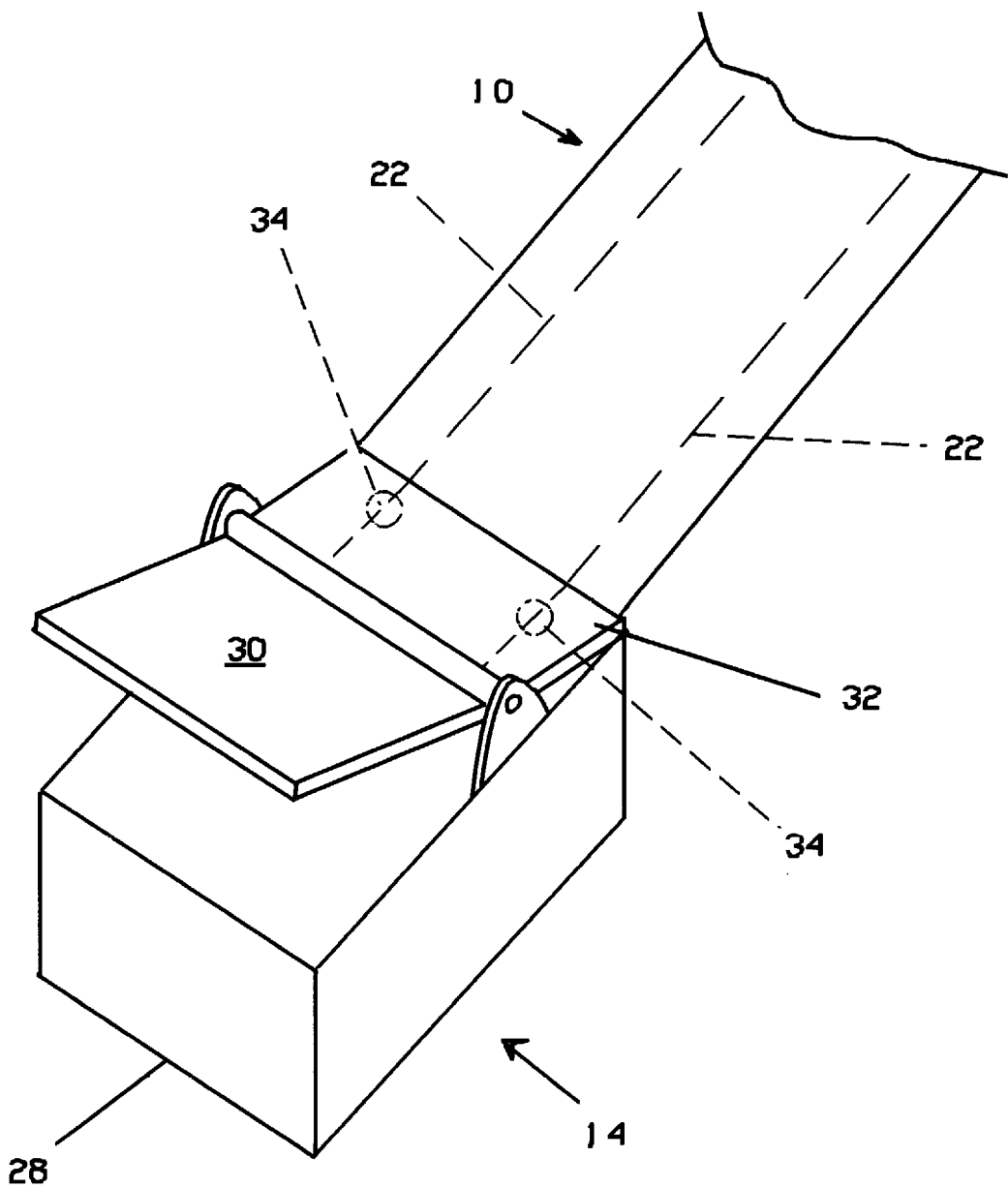
FIG. 4 is an illustration showing construction details of an exterior of an indicator unit 14.
Figure 4A:
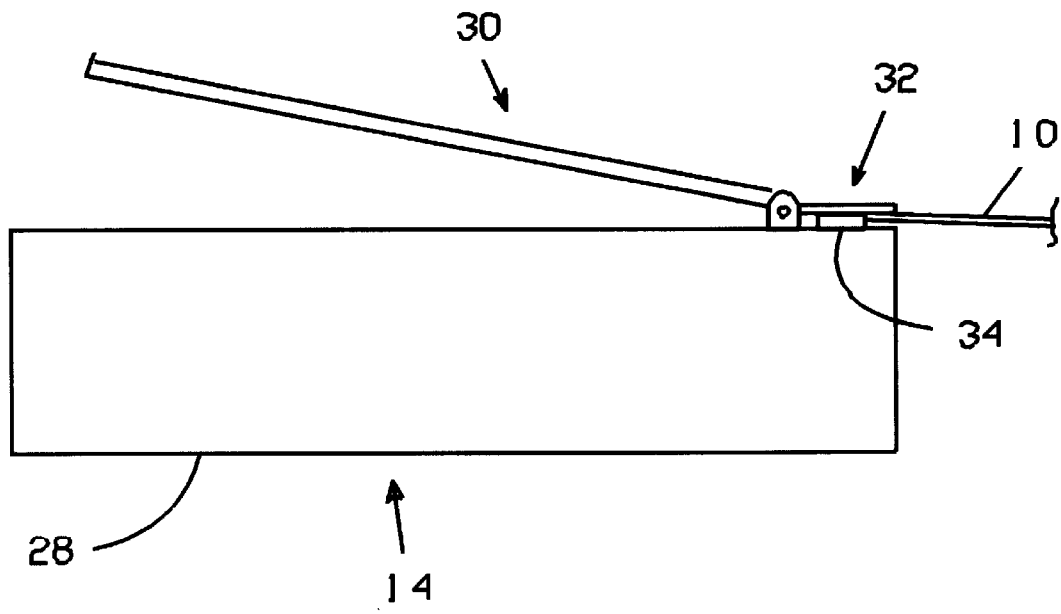
FIG. 4a is an illustration of additional exterior construction details of the indicator unit 14.
Figure 4B:
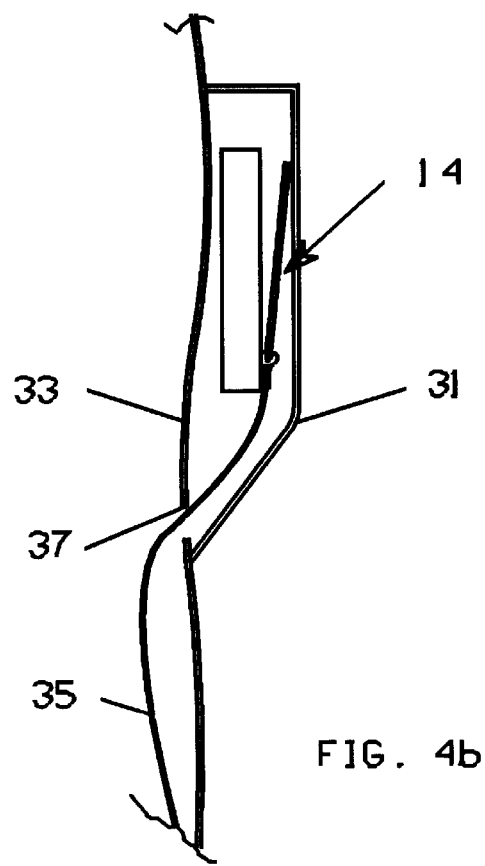
FIG. 4b is a broken away view of indicator unit 14 placed in a pocket of a user.
Figure 4C:
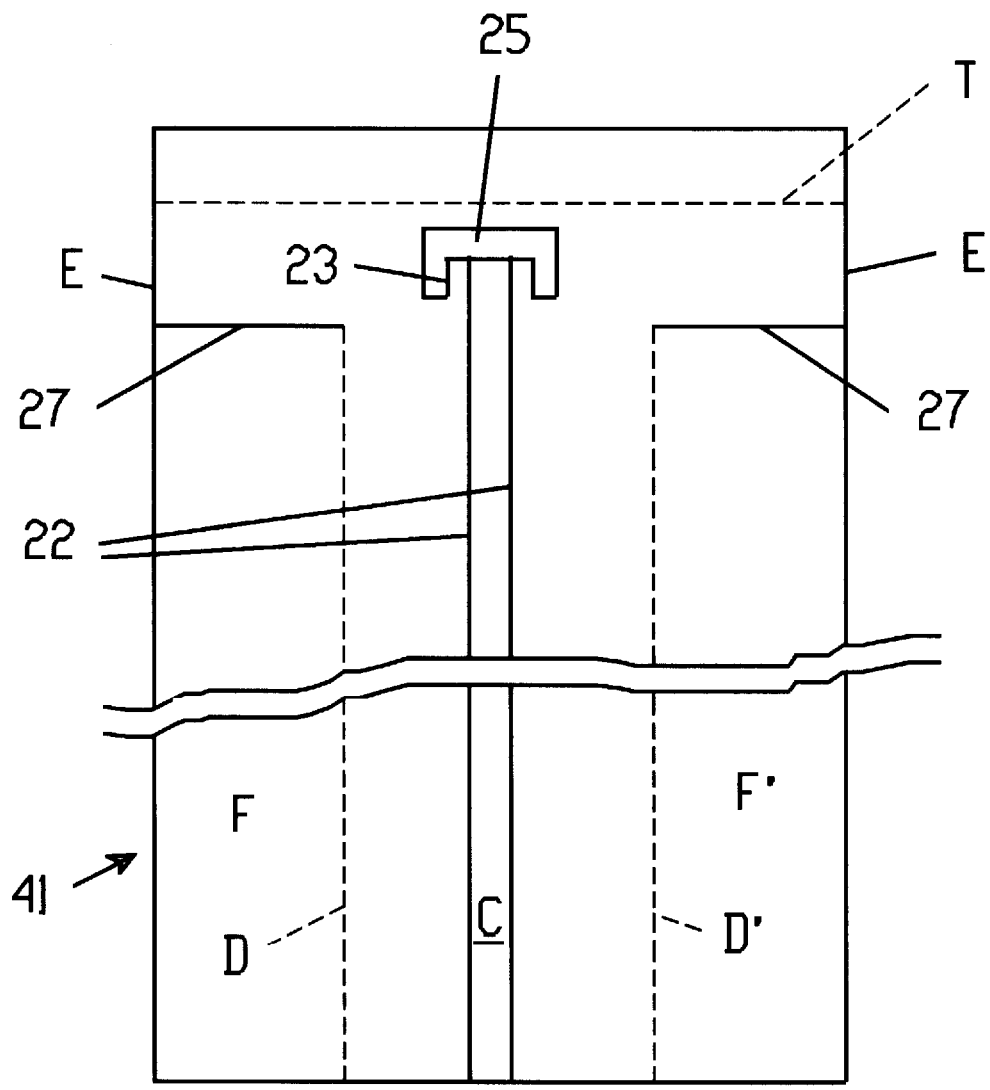
FIG. 4c is another embodiment of a sensor strip wherein a pocket for the indicator unit is formed at one end of the sensor strip.

In an alternate embodiment of the strip 10 as shown, reference is made to FIG. 4c. In this embodiment, a widened strip 41 is constructed with sensing threads 22 terminating at a tongue 23 positioned in an inverted U-shaped cutout 25. Transverse cuts 27 are made as shown on either side of the depending legs of cutout 25 to form downwardly extending flaps F and F', with flap f folded along dashed lines D behind center region C, and flap F' folded along dashed lines D' over center region C. Edges of flaps F and F' are then attached to the center region C, enclosing threads 22 so that they cannot come into contact with skin of a user. Above cutout 25, the upper region is transversely folded along dashed line T over cutout 25, and edges E thereof folded and attached together to form a pocket 27 (FIG. 4d) for receiving unit 14. Constructed as described, tongue 23, being inside the pocket, is clipped to unit 14 as described above, with unit 14 resting in the pocket, which simply hangs outside an incontinence garment 29 inverted from a position shown in FIG. 4c.

Circuitry 14 is a microcontroller based circuit energized when urine or wet fecal material bridges the sensor element, and provides a number of operational modes responsive thereto. These modes include an audio indicator, a blinking LED light, a vibratory indication, and transmission of an RF signal to a receiver that alerts staff of a care-giving institution to a situation requiring changing of an incontinence garment. Significantly, the audio indication may be configured to incorporate a conveniently replaceable or re-recordable voice module which delivers a message usable for training purposes, which may be related to enuresis (nightime wetting), incontinence, or other types of training when incorporated in other devices, as will be further explained.

Referring to FIGS. 4 and 4a, the housing 28 and method of attachment of a sensing strip 10 to unit 14 is shown. As described above, a spring-biased clip 30 on unit 14 releasably secures a strip 10 under a clamping region 32, with contacts 34 set in housing 28 providing electrical engagement between the circuitry of unit 14 and threads 22. Additionally, clamping region 32, which bears against contacts 34 and possibly housing 28 may be constructed with teeth or an abrasive area so that strip 10 is more securely held by clamping region 32. As such, unit 14, being exceedingly small and lightweight, may simply hang by the sensor strip secured only by clamping region 32. In the instance where the users are able to care for themselves, unit 14 may be placed in a pocket of a garment via an opening in the interior pocket lining as described above, with sensing strip 10 being of a length so as to permit such location. This eliminates the need for pockets in the incontinence garment or sensing strip and/or cumbersome mounting arrangements for unit 14 as evident in the prior art. In addition, housing 28 of unit 14 is of sealed, waterproof construction so as to prevent any leakage of urine to the interior of unit 14. As such, LED indicators may be sealed by a waterproof compound, such as a silicone sealant, and a sound element, such as a piezoelectric or conventional audio transducer, or moisture-proof speaker, may be mounted behind small openings or a small grille isolated by a sheet material, such as a waterproof plastic positioned between the transducer and interior of housing 28. In the instance where a widened sensing strip is used, the end of the strip may be folded longitudinally so that threads 20 are aligned with contacts 34.

Figure 5:
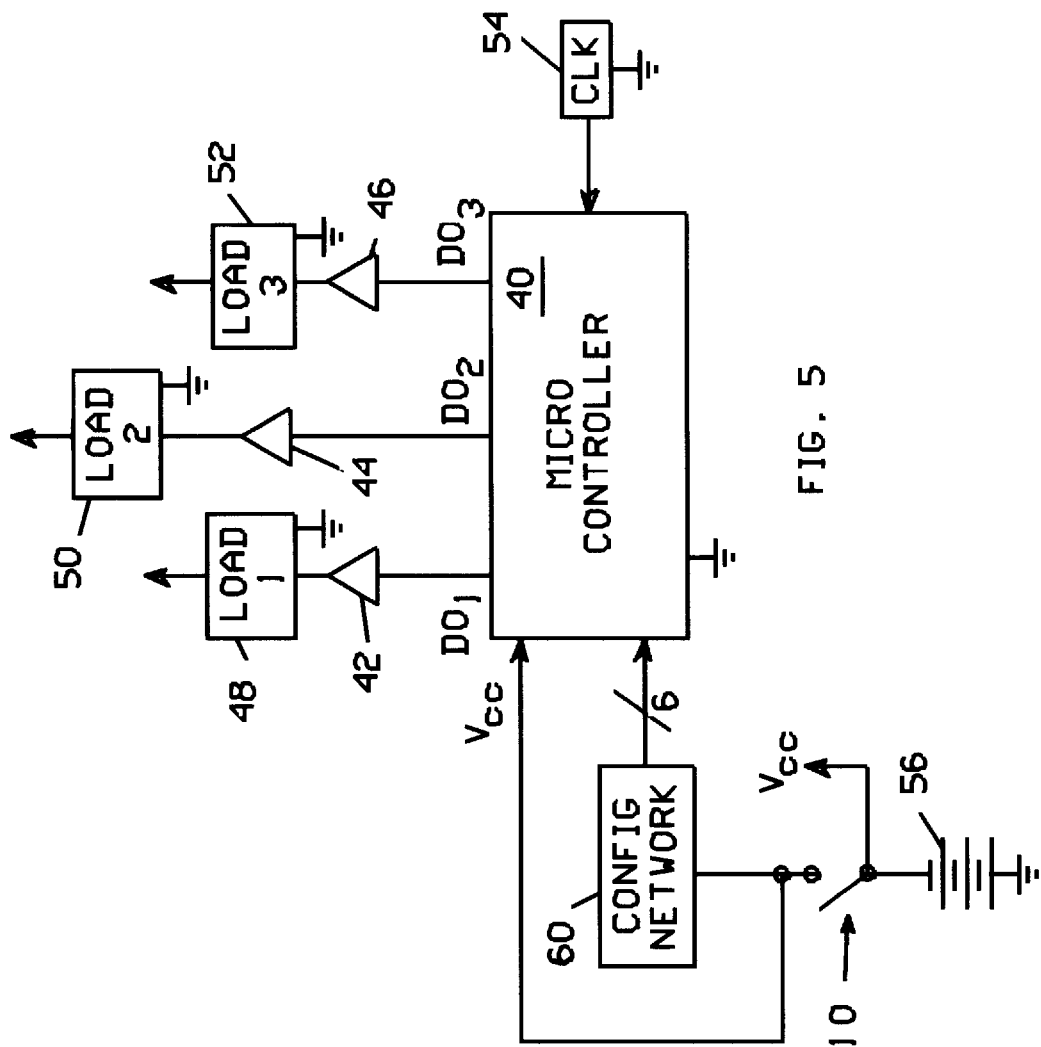
FIG. 5 is a block diagram of indicator unit 14.

Referring now to FIG. 5, a block diagram of a microcontroller-based system is shown which controls electrical operation of the instant invention. Here, three outputs 48, 50, and 52 labeled load 1, load 2, and load 3 are shown for a microcontroller which may implement at least five instructional modes of operation to indicate wet or saturated conditions of an incontinence garment. These outputs may be coupled to activate a vibrator for providing vibration, an audio transducer for providing an audible signal, or a visible indicator for providing a visible indication, such as an LED indicator. Additionally, an RF transmitter may be energized responsive to a wet condition of the incontinence garment to transmit an RF signal to a receiver or receivers located at a centralized location or on a care-givers person. Further, one of the three outputs may be used to actuate a pre-recorded voice memory module which may be of various time durations, this module removable from unit 14 and being interchangeable with other voice modules having different messages recorded thereon.

As stated, unit 14 may be based on a microcontroller 40 (FIG. 5), such as one of the PIC16C family of microcontrollers, manufactured by MICROCHIP, located in Chandler, Ariz. These microcontrollers have up to 2K bytes of ROM memory, which may be used to store a system program, and up to 72 bytes of RAM memory, which may be used to store program variables during timing operations. Additionally, as this microcontroller family is of CMOS technology, its low power consumption (less than 2 ma at 5 VDC clocked at 4 Mhz) is ideal for battery powered applications. In this embodiment, it is contemplated to power unit 14 with a 6 volt battery such as one of those found in powering photography equipment, as should be apparent to those skilled in the art. As described, data outputs DO1, DO2, and DO3 of microprocessor 40 may be used to activate, via buffer amplifiers 42, 44, and 46, a first load 48 which may be an electric vibrator motor, a second load 50 which may be an audio transducer, and a third load 52 which may be an LED indicator, respectively. Alternately, one of loads 48, 50, and 52 may be replaced by an RF transmitter so as to transmit a signal to a receiver located at either a centralized location or on the person of a caregiver, and another of loads 48, 50, and 52 may be replaced by the electronic voice module. An oscillator 54 provides a train of clock pulses to microcontroller 40 at any rate up to about 20 Mhz, with about 3.5 Mhz being typical. Sensing strip 10 is depicted as a switch, which is closed by urine or fecal material bridging the threads in strip 10, providing power from battery 56 to configuration network 60, microcontroller 40 and other components requiring power. The switching action of strip 10 occurs due to urine being rich in electrically conductive electrolytic compounds. Network 60, which is coupled to data input lines of microcontroller 40, is configured to activate particular ones of data outputs DO1, DO2, and DO3 for selected time intervals.

Figure 6:
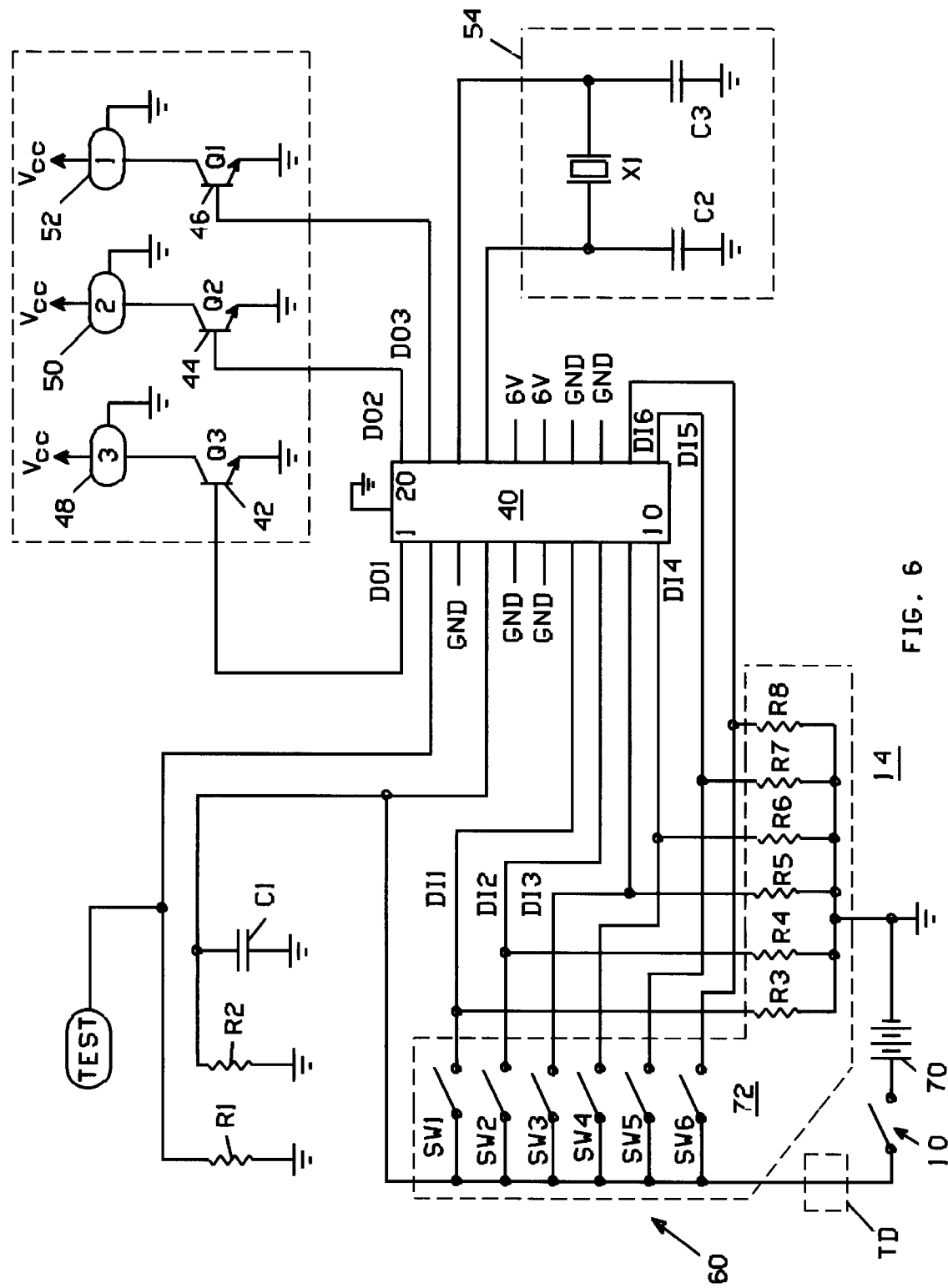
FIG. 6 is a schematic diagram of the block diagram of FIG. 5.

Referring now to FIG. 6, a detailed schematic of the block diagram of FIG. 5 is shown. In this schematic, it is seen that, upon closure of strip switch 10 by urine or fecal material, power and a reference ground potential are provided by battery 70 to microcontroller 40 and all components requiring such potentials. Here, battery power is applied to one conductive thread of sensing strip 10, with the other conductive thread of strip 10 coupled to configuration network 60, the power input of microcontroller 40, and distributed to other components requiring power. Network 60 may include a DIP switch 72 incorporating 6 switches coupled between the switched conductor of sensing strip 10 and a respective one of data inputs DI1–DI6 of microcontroller 40. Coupled between each of DIP switches 72 and the ground reference potential are resistors R3–R8, which serve to develop a voltage drop sufficient to trigger the respective inputs of microcontroller 40. Here, where a higher value of resistance is selected for resistors R3–R8, less current flow through sensing strip 10 would be sufficient to trigger the respective inputs of microcontroller 40, and conversely, where a lower value for these resistors is selected, more current flow would be required through strip 10 in order to develop a sufficient voltage drop to trigger the inputs of microcontroller 40. Thus, sensitivity of the system may be adjusted by varying resistances of resistors R3–R8. By way of example, these resistors may be in the range of about 100K ohms, this selection being fairly sensitive to spilled urine on strip 10 and very conservative of battery power. Alternately, in place of battery 70, an oscillating or other signal may be applied to one of the conductive threads of sensing strip 10, with the other thread coupled to a detector for detecting the oscillating signal when threads 20 are bridged by conductive material. A HIGH logic level would then be provided to network 72 by the detector, activating the loads as described. Also, in the instance where an individual is dribbling as described above, an adjustable time delay TD (dashed lines) may be located between strip switch 10 and the rest of the circuitry associated with the microcontroller so that upon expiration of the time delay, power is applied to the microcontroller and a HIGH logic level applied to network 72. Alternately, a slower clock pulse may be used in conjunction with a counter and latching decoder to implement the time delay, with the decoder providing a latched output to power the microcontroller and switches 72 responsive to a selected count. As such, and with closure of selected ones of switches 72, when the conductors of sensing strip 10 are shorted by urine or wet fecal material, configuration information is provided to microcontroller 40 through DIP switches 72, this configuration information controlling sequencing and duration of outputs DO1, DO2, and DO3. The program loaded in ROM memory of microcontroller 40 may use data inputs DI1–DI3 to select which of loads 48, 50, and 52 are to be activated, respectively, with data inputs DI4–DI6 selecting time delays and sequencing of activation of the loads. Constructed as described, and with 6 switches 72, 16 distinct operating modes are made available to the user. The three outputs DO1, DO2, and DO3 may be normally LOW with a common ground, and when activated by the microcontroller, will transition HIGH, enabling the respective one of loads 48, 50, and 52 through a respective buffer amplifier. Where time delay functions are enabled, delays of up to three hours may be selected in one hour increments, after which sequencing of the loads is initiated. After the program sequencing the loads is completed, the microcontroller is placed in a "sleep" mode in order to conserve battery power.

As described, loads 48, 50, and 52 are activated by data lines DO1 controlling load 1, DO2 controlling load 2, and DO3 controlling load 3 via buffer amplifiers 42, 44, and 46, respectively. By way of example, load 48 may be a vibrator, load 50 may be an audio signal, and load 52 may a be LED indicator. In the latter instance, a LED having an internal current-limiting resistor or internal circuitry for causing the LED to blink may be used, or an external current-limiting resistor (not shown) may be used. Alternately, one of the loads may be coupled to a short-range 902–928 Mhz Industrial, Scientific, and Medical (ISM) RF transmitter and which may use multiple frequencies in this range, for notifying caregivers having miniature receivers that a patient has a wetted or soiled garment. Additionally, a computer may be activated by these transmissions in order to record times and dates of instances of incontinence. Inasmuch as space in unit 14 having an RF transmitter is a prime consideration, frequency control devices of layered construction may be arranged in one miniaturized package so that minimal printed circuit board space is required for transmitters that transmit over as many as 5 discrete frequency bands. Such layered frequency control devices are custom manufactured by NPI of Huntsville, Ala.

Figure 7:
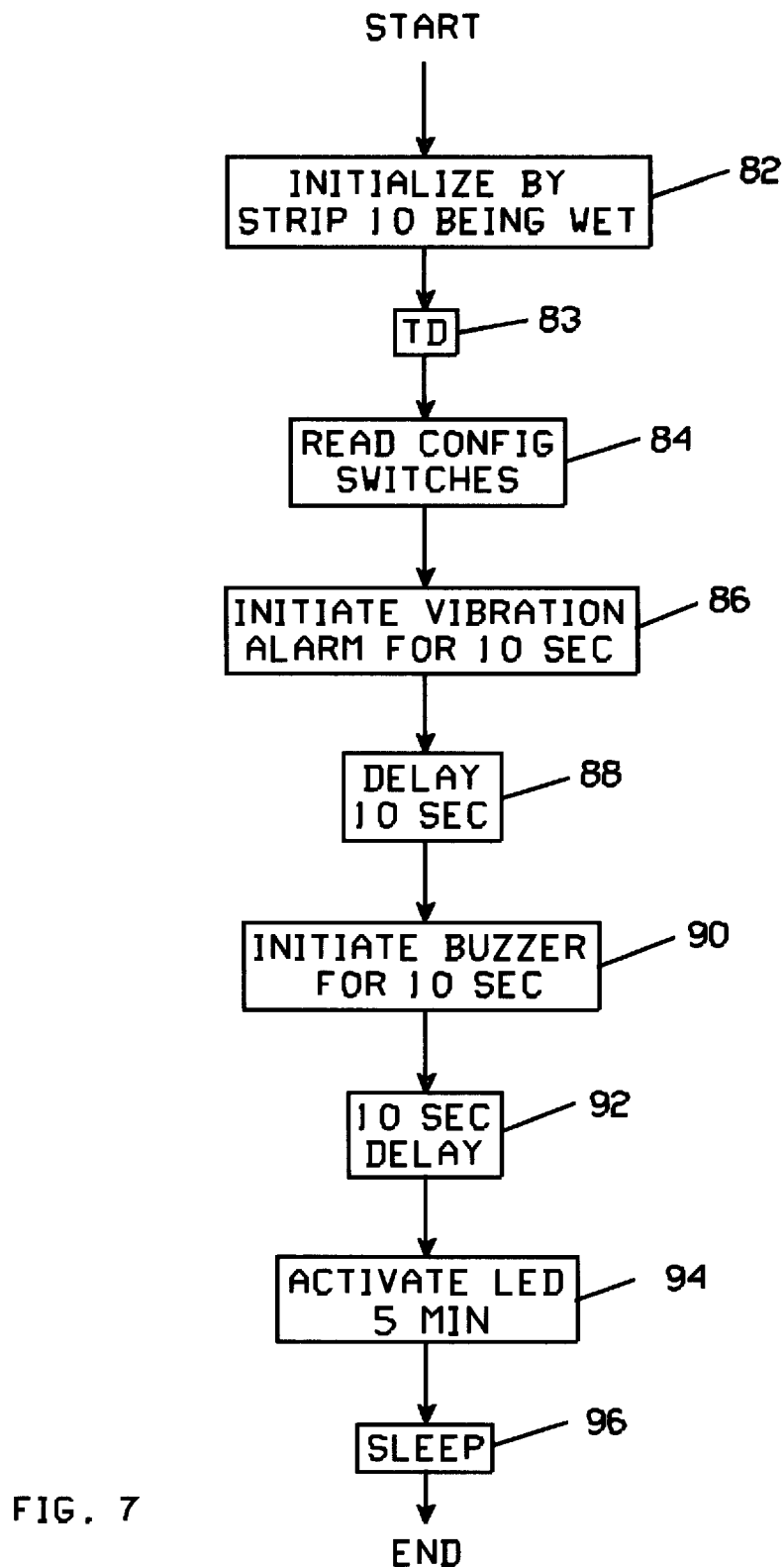
FIG. 7 is a flowchart of one embodiment of a program used to operate unit 14.

The ROM memory of microcontroller 40 is loaded with a program, which may be written in RISC (reduced instruction set computer) language to perform the various functions of the system, an example of one program being shown in the flowchart of FIG. 7. Here, unit 14 is unpowered until sufficient urine is spilled to bridge conductive threads 20, effectively closing sensor switch 10 as shown at box 82. This feature greatly conserves battery power; the circuitry contained in package 14 being unpowered until switch 10 is closed. When energized, microcontroller 40 is initialized as indicated at box 82, clearing and initializing all registers to a predetermined value as is known to those skilled in the art. After power-up initialization of microcontroller 40, the program directs configuration switches 72 to be read at box 84, and an output or outputs to the loads provided based on the settings of configuration switches 72. As shown at box 86, load 48, which may be a vibrator motor, may be initially energized to provide a silent, vibratory indication that alerts a person capable of caring for himself/herself to the fact that his/her incontinence garment has been wetted or soiled. After a duration which may be about 10 seconds or so, the vibration motor is de-energized, and a time delay of about 10 seconds or so is initiated at box 88. After the delay at box 88 expires, the program proceeds to box 90 where load 50 is energized, which load may be an audio signal such as a buzzer, which may be energized for about 10 seconds, after which another time delay of about 10 seconds may be initiated at box 92. After the time delay of box 92 expires, the program proceeds to box 94 where load 52, which may be an LED indicator, is energized for a duration which may be about 5 minutes or so. After this delay expires, the program directs microcontroller 40 to enter a power-conserving sleep mode, as indicated at box 96. Upon changing the incontinence garment and sensing strip 10, power is removed from microcontroller 40, resetting controller 40 in preparation for the next cycle. This type of program may be used where an individual is bedridden, but able at least at times change his/her own incontinence garment responsive to the vibrating indication. In the instance where a person has a "dribbling" problem, after the sensing strip becomes wet, a time delay TD, at box 83 in the flowchart of FIG. 7, may be started, and which may last any duration selected by the user to allow the incontinence garment to become sufficiently wet to warrant changing. After expiration of the time delay of box 83, the program proceeds to sequence the loads as described for FIG. 7.

In the instance where an individual is ambulatory and capable of carrying out the tasks of everyday life, such as being employed, the individual may not need an audible indication due to embarrassment it may cause. In this instance, the vibration indicator and/or the LED indicator may be coupled to a respective one of the outputs of microcontroller 40, and activated as described for a selected period of time as determined by switches 72 and the program stored in ROM memory. The audible indication may be disabled by opening or closing the appropriate ones of switches 72.

Figure 8:
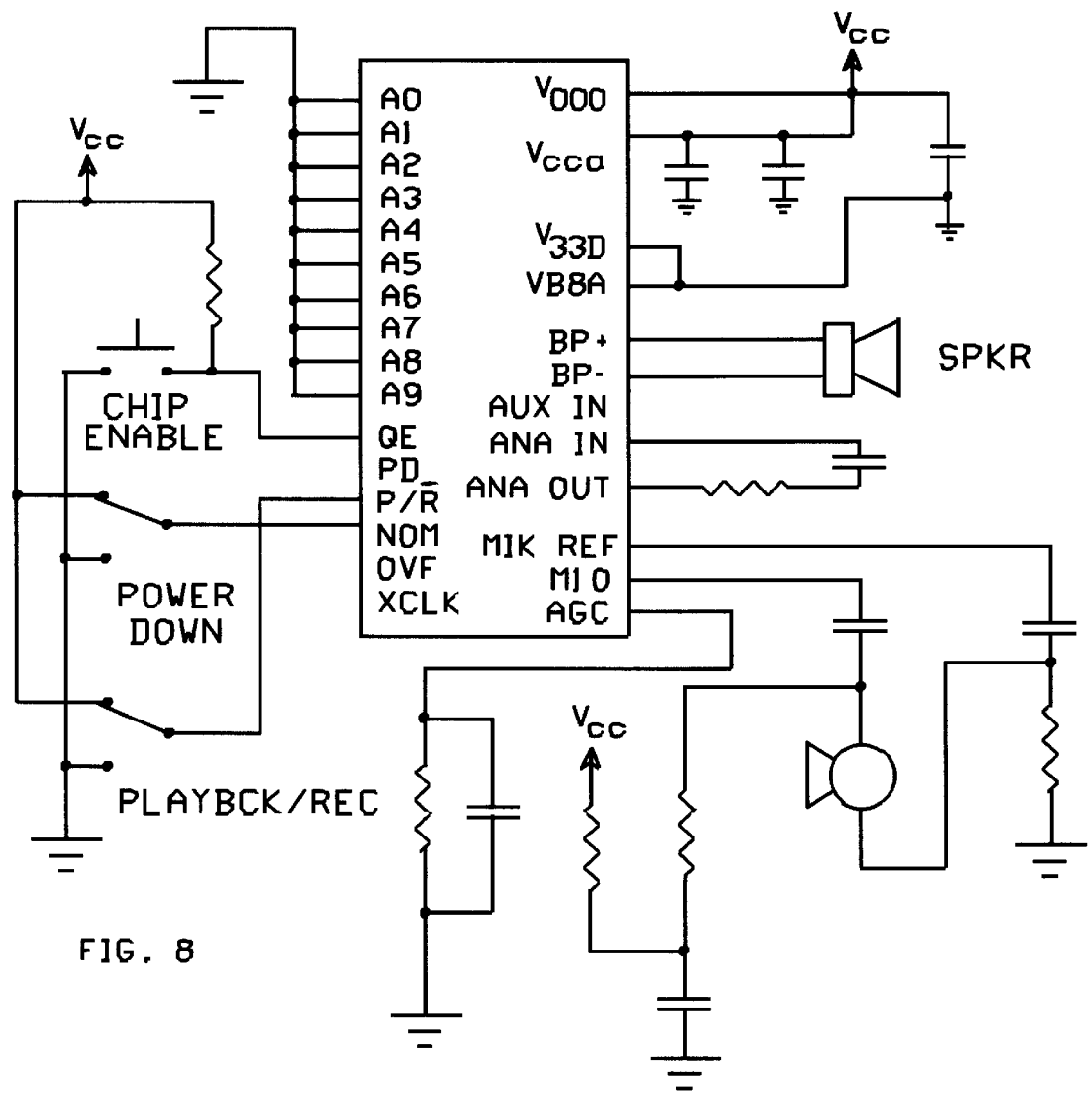
FIG. 8 is a schematic diagram of a voice module of the instant invention.

With respect to the voice module discussed above, reference is made to FIG. 8. Here, the voice module may be based upon a single chip record/playback device such as one of the ISD 2500 series devices available from INFORMATION STORAGE DEVICES of San Jose, Calif. These devices record and store up to 90 seconds on a single integrated circuit, these integrated circuits capable of being "daisy chained" together to record and play back longer messages. The circuitry of FIG. 8 may be incorporated permanently into electronic package 14, or it may be incorporated into a removable module 120 as shown in FIG. 9. Module 120 may be held in place in socket 122 by any means as would be known to those skilled in the art, and is provided with an appropriate number of contacts 124 (only 4 shown) as required to transfer the appropriate signals to module 120 from unit 14. Unit 14 in turn provided with a corresponding number of contacts 126 coupled to the circuitry of FIG. 6 which in turn activates the voice circuitry of FIG. 8 at the appropriate time depending on the settings of switches 72.

While voice module 120 is shown used in conjunction with unit 14, which monitors incontinence, module 120 may be used in a wide variety of devices where it is desired to provide a voice message responsive to activation of the device. Here, instead of being triggered by sensor strip 10, the voice module may be triggered by activation of a device or proximity switch. For instance, unit 14 may be the base of a toothbrush, which receives a prerecorded voice module 120 providing a message of a duration corresponding to a length of time brushing should be performed. For children, this message may be of an entertaining or instructional nature, such as how brushing of teeth should be done or a recitation of the multiplication tables. In this instance, where the module contains an educational message such as the multiplication tables, when a particular multiplication table is learned, such as the "times one" table, the module may be removed and either a different module containing the "times two" table inserted into socket 122 or the original module containing the "times one" table rerecorded with the "times two" table. Another application of such a system would be construction of the voice module in medical home-use devices such as a home glucose monitor commonly used by diabetics, the module providing instructions such as how to use the monitor and possibly what the user should do to treat instances of high or low blood sugar. In this instance, and where the glucose monitor provides an indication of high or low blood sugar, the appropriate instructions may be in response to the indication. For example, an indication of high blood sugar may elicit the message of "Your blood sugar is too high, take insulin now." or some other instructional message. Additional applications include instructional or promotional messages related to grocery products, which messages being prerecorded and packaged in conjunction with a proximity switch within a grocery store so that when a customer activates the proximity switch, the message is played. A similar use may be found in car sales lots where a voice module triggered by a proximity switch may be located in or on an automobile, and delivers a message containing details related to the car that is for sale. Also included would be specific messages for individuals trying to quit smoking cigarettes or maintain certain body weights. Here, specific or progress instructional messages may be developed by health institutions. Other applications include golf instructions relating to an individual or specific hole of a particular course; blood pressure control with specific instructional messages, chiropractors offering home program therapy through specific individual progress messages, and all other applications where such prerecorded messages would be useful or necessary.

In yet another embodiment of the invention, and referring to FIG. 10, the microcontroller circuitry of FIGS. 5 and 6 may be incorporated into a fishing lure. Here, the circuitry may be constructed so as to be fitted into a cylindrical housing 150, the cylindrical housing in turn being insertable into a soft flexable lure such as a frog or fish. Contacts 152 corresponding to the conductive threads of sensor strip 10 are provided on the exterior of the cylinder in a location that would be exposed to water so that the circuitry becomes activated when the lure is thrown into a river, lake, etc. A removable threaded cap 154 in conjunction with an O-ring seal may be used to sealably enclose a battery compartment, which may receive a 6 volt battery as described above, an N-sized alkaline battery, a AAA sized battery, or a plurality of wristwatch-type batteries. When activated, the program may be configured to energize one or more LEDs 156, a piezoelectric buzzer 158, and a vibrator located inside cylinder 150. Any sequence may be used for the LEDs, buzzer and vibrator, such as one wherein the LEDs are illuminated in a blinking mode for about 5 seconds followed by a 10 second delay. The vibrator may then be activated for about 2 seconds, followed by another 10 second delay after which the buzzer may be activated for about 3 seconds. A longer delay may then be provided, such as 30–40 seconds, after which the program repeats until battery power is removed by removing the lure from the water. Alternately, the circuitry may be incorporated into a lure such as a "plug"-type lure without being removable, as should be apparent to one skilled in the art. Further, effectiveness of the lure may be enhanced by the electrical field generated by current flowing between contacts 152, it being understood that certain game fish are sensitive to such electrical fields.

Having thus described my invention and the manner of its use, it is apparent that incidental changes may be made thereto that fall within the scope of the following appended claims, wherein we claim:

1. An incontinence training system comprising:
   a rectangular pad of sheet construction covering the urogenital area of a user, said pad further comprising:
      a pocket at one end of said pad,
      first and second sensor threads positioned lengthwise in spaced relation in said pad, said threads comprising an electrically conductive material, with ends of said first and second sensor threads extending into said pocket, and opposite ends of said threads terminating near an opposite end of said pad,
   an indicator unit in said pocket and connectable to said ends of said first and second sensor threads, said indicator unit further comprising:
      a microcontroller containing a storage register provided with instructions so that said indicator unit is operable to provide a signal responsive to said sensor threads being bridged by body fluids containing electrolytes.

2. A system as set forth in claim 1 wherein said signal includes, in a predetermined sequence and for predetermined time intervals, a vibration signal, an audible signal, and a visible signal.

3. A system as set forth in claim 2 wherein said vibration signal persists for about 5 seconds, followed by a pause of about 5 seconds, after which said audible signal persists for about 5 seconds, followed by a pause of about 5 seconds, after which said visible signal persists for about 5 minutes, followed by said indicator unit being placed in a standby mode.

4. A system as set forth in claim 1 wherein said indicator unit provides said vibration signal for about 10 seconds, after which said indicator unit is placed in a standby mode.

5. A system as set forth in claim 1 wherein said indicator unit is configured as an audio recorder and playback device, with a playbeck mode thereof responsive to said sensor threads being bridged by said body fluids.

6. A system as set forth in claim 1 wherein said signal further comprises a vibration signal, a visible signal, and an audible signal.

7. A system as set forth in claim 6 wherein after expiration of a predetermined period of time, said signal is terminated and said indicator is placed in a standby mode of operation.

8. A system as set forth in claim 6 wherein said indicator unit is reset and enabled for operation when said sensor threads of a said pad containing body fluids are disconnected from said indicator unit.

* * * * *